United States Patent [19]

Crochemore

[11] Patent Number: 4,622,426

[45] Date of Patent: Nov. 11, 1986

[54] PREPARATION OF N,N'-BIS(2-HYDROXYETHYL)OXAMIDE

[75] Inventor: Michel Crochemore, Chaponost, France

[73] Assignee: Rhone-Poulenc Specialites Chimiques, Courbevoie, France

[21] Appl. No.: 670,062

[22] Filed: Nov. 9, 1984

[30] Foreign Application Priority Data

Nov. 9, 1983 [FR] France ............................. 83 18077

[51] Int. Cl.$^4$ .................... C07C 102/06; C07C 103/38
[52] U.S. Cl. .................................. 564/135; 564/134; 564/136; 564/160
[58] Field of Search ................ 564/136, 160, 134, 135

[56] References Cited

U.S. PATENT DOCUMENTS 2,857,390 10/1958 Kirchner ........................ 564/160 X
3,543,306 11/1970 Biland ............................ 564/160 X

OTHER PUBLICATIONS

Stuart et al., *Can J. Res.* 26, pp. 402–409, (1948).
Desseigne, *Revue des Poudres*, 30, p. 101, (1948).
Knorr et al., *Chem. Ber.*, 36, pp. 1278–1279, (1903).
Rauscher et al., *J. Am. Chem. Soc.*, 70, p. 438, (1948).
Phillips, *J. Am. Chem. Soc.*, 73, pp. 5557–5559, (1951).
D'Alelio et al., *J. Am. Chem. Soc.*, 59, pp. 111–112, (1937).
Wagner et al., *Synthetic Organic Chemistry*, pp. 568–569, (1953).

*Primary Examiner*—Charles F. Warren
*Assistant Examiner*—Carolyn S. Greason
*Attorney, Agent, or Firm*—Burns, Doane, Swecker & Mathis

[57] ABSTRACT

N,N'-bis(2-hydroxyethyl)oxamide is facilely prepared, e.g., in finely divided crystalline form, by reacting an alkyl oxalate with ethanolamine in an aqueous reaction medium.

11 Claims, No Drawings

PREPARATION OF N,N'-BIS(2-HYDROXYETHYL)OXAMIDE

BACKGROUND OF THE INVENTION

1. Field of the Invention:

The present invention relates to the preparation of N,N'-bis(2-hydroxyethyl)oxamide by reacting ethanolamine with an alkyl oxalate in an aqueous reaction medium.

2. Description of the Prior Art:

N,N'-Bis(2-hydroxyethyl)oxamide is a known compound which is useful, e.g., as an intermediate in the manufacture of powerful explosives [cf. M. G. Desseigne, *Revue des Poudres*, 30, page 101 (1948) and R. S. Stuart et al, *Can. J. Res.*, 26, page 402 (1948)]. N,N'-Bis(2-hydroxyethyl)oxamide is typically prepared by condensing ethanolamine with a dialkyl oxalate. Since publication in L. Knorr and P. Rossler, *Ber.*, 36, pages 1278–1279 (1903) this condensation has been carried out in an anhydrous reaction medium, either in the absence of solvent or employing an excess of ethanolamine, or in anhydrous alcohol; cf. A. P. Phillips et al, *J. Am. Chem. Soc.*, 73, page 5557 (1951), G. F. D'Alelio et al, *J. Am. Chem. Soc.*, 59, page 111 (1937), R. S. Stuart et al, *loc. cit.*, and M. G. Desseigne, *loc. cit.* These latter authors have emphasized the need to employ anhydrous solvents as reaction media, in particular alcohols such as ethanol and butanol. Best yields of N,N'bis(2-hydroxyethyl)oxamide are obtained when alcohols are employed as solvents. In this case, yields based on oxalate or ethanolamine exceed 90% and can be quantitative. In spite of the immediately aforesaid, such processes suffer from two major disadvantages which make them impracticable on an industrial level. The first of these disadvantages relates to the productivity of the reaction, which is found to be particularly low and on the order of 110 kg/m$^3$ of reaction medium, in the best of cases. Furthermore, it has also been found that, when an alcohol is used as the reaction solvent, the N,N'-bis(2-hydroxyethyl)oxamide precipitates as it is being produced in the form of finely divided, alcohol-swollen particles, which results in the formation of a non-fluid cream which adheres to the reactor walls. This cream is quite difficult to remove from the reaction apparatus and to filter off. Preparation of N,N'-bis(2-hydroxyethyl)oxamide on an industrial scale consequently has entailed the use of a reaction medium as free as possible from the aforementioned disadvantages but which nevertheless provides good yields.

SUMMARY OF THE INVENTION

Accordingly, a major object of the present invention is the provision of a still further improved process for preparing N,N'-bis(2-hydroxyethyl)oxamide by reacting an alkyl oxalate with ethanolamine, which improved process is even more conspicuously devoid of those disadvantages and drawbacks characterizing the state of this art, and which features the use of water as the alkyl oxalate/ethanolamine reaction medium.

DETAILED DESCRIPTION OF THE INVENTION

More particularly according to the present invention, it has now unexpectedly been determined that when an alkyl oxalate is reacted with ethanolamine in an aqueous reaction medium, the concentration of said reactants can be appreciably higher than in an alcoholic reaction medium. This results in a substantial increase in process productivity, up to the order of 400 kg/m$^3$ of reaction mixture. Moreover, the N,N'bis(2-hydroxyethyl)oxamide crystallizes as it is formed in said aqueous reaction medium, in crystalline form, and thus can instantly and readily be separated therefrom by filtration.

Such good yields and ease of separation fly in the face of the prior art which has mandated the use of anhydrous solvents as reaction media.

The selection of the starting material alkyl oxalates is not critical and any oxalate based on aliphatic alcohols may be employed. In practice, it is preferable from an industrial point of view to use the oxalates of the lower aliphatic alcohols, such as methyl, ethyl, n-propyl, isopropyl or n-butyl oxalates.

The amount of ethanolamine, expressed in moles per mole of oxalate, is advantageously close to the stoichiometry of the reaction, namely, 2 moles per mole of oxalate. Obviously, use of a stoichiometric deficit or excess of ethanolamine remains within the ambit of the present invention; however, such would not result in any particular advantages.

The temperature at which the reaction is carried out may vary over wide limits. It may advantageously range from 0° to 100° C. However, excellent results are obtained by carrying out the reaction at a temperature of 15° to 50° C. It typically suffices for the temperature to be on the order of 20° to 40° C.

The concentration of the reactants in water is not critical, but it is not desirable to carry out the reaction in a medium which is too dilute if good reaction productivity is to be maintained. In this respect, it is preferable, in practice, that the concentration of ethanolamine in water should be equal to at least 2.5 moles/liter and more preferably at least 5 moles/liter. The maximum concentration depends upon the stirrability of the reaction mixture.

From a practical standpoint, the oxalate should be gradually added to the aqueous solution of ethanolamine as the reaction proceeds. Operating in this manner avoids hydrolysis of the oxalate. The period of addition depends upon the reaction conditions: temperature, dilution and efficiency of stirring.

The N,N'-bis(2-hydryoxethyl)oxamide precipitates in the form of fine crystals immediately as it is formed. In this manner a product of very high purity is obtained, which can instantly be filtered. The filtrate, which consists of an aqueous solution of N,N'-bis(2-hydroxyethyl)oxamide, alcohol originating from the condensation and possibly alcohol from washing of the precipitate, is distilled to remove the alcohol. The aqueous solution of N,N'-bis(2-hydroxyethyl)oxamide which is thus recovered is preferably cycled to a new condensation reaction.

In order to further illustrate the present invention and the advantages thereof, the following specific examples are given, it being understood that same are intended only as illustrative and in nowise limitative.

EXAMPLE 1

Into a 1-liter glass flask fitted with a thermometer, a semicircular stirrer and a dropping funnel, and cooled with a cold water bath, were added 200 ml of distilled water and 183 g (3 moles) of ethanolamine. The mixture was stirred and an aqueous solution of ethanolamine was obtained, the temperature of which reached 35° C. This solution was cooled to 25° C. and then 219 g (1.5 mole) of ethyl oxalate were added over 1 hour under stirring while the temperature was maintained at 25° C.

following Table, which also reports the results obtained:

TABLE

| EXAMPLES | REACTANTS | | WATER | T | DURATION (hours) | | OXAMIDE | | R.Y. % | |
|---|---|---|---|---|---|---|---|---|---|---|
| | Amine | Oxalate | (in ml) | (°C.) | Addition | Completion | Isolated | Dissolved | Isolated | Total |
| 3 | 122 g | 146 g | 400 | 25° | 2 h | 2 h | 112 | 21 | 63.6 | 75.5 |
| 4 | 122 g | 146 g | 200 | 25° | 2 h | 2 h | 140 | 12 | 79.5 | 86.5 |
| 5 | 183 g | 219 g | 200 | 25° | 2 h | 2 h | 219 | 24 | 83 | 92 |
| 6 | 183 g | 219 g | 200 | 80° | 2 h | 1 h | 194 | 13.5 | 73.5 | 80.5 |

Crystallization of N,N'-bis(2-hydroxyethyl)oxamide began when a third of the oxalate had been added. The reaction mixture was maintained stirred at 25° C. for 15 minutes upon completion of the addition. The contents of the flask were cooled to 3° C. and filtered through a glass sinter. Filtration was instantaneous. The filter cake was washed with 150 cm$^3$ of absolute alcohol and dried under vacuum at 50° C. to constant weight.

This procedure yielded 220 g of a product having a melting point (Kofler bench) of 169° C. and which assayed at 100% of N,N'-bis(2-hydroxyethyl)oxamide by liquid chromatography under pressure. The identity and the purity of the product were confirmed by IR, NMR and mass spectrometry.

In addition 445 cm$^3$ of mother liquors were recovered, which were determined by analysis to contain 24 g of N,N'-bis(2-hydroxyethyl)oxamide in solution. A total of 244 g of oxamide had thus been produced, which corresponds to a yield of 92% based on the ethanolamine and oxalate employed. The yield (R.Y.) of isolated pure product was 83%.

EXAMPLE 2

A first experiment was carried out by repeating the operating procedure described in Example 1. After filtering off and washing the cake, the filtrate and the alcohol wash were combined and then the wash alcohol and the reaction alcohol were distilled at atmospheric pressure with the aid of a Vigreux column 220 mm high and 24 mm in diameter. 3,012 cm$^3$ of 95% alcohol were collected as distillate, and 145 cm$^3$ of an aqueous solution of N,N'-bis(2-hydroxyethyl)oxamide, which were charged into the reaction flask. The condensation was repeated with a fresh addition of 183 g of ethanolamine and then 219 g of ethyl oxalate, and the reaction mixture was then treated as before, the cake being washed with the recovered alcohol. The operation was repeated 5 times. A total of 1,314 g of ethyl oxalate (9 moles) and 1,098 g (18 moles) of ethanolamine had been charged. A total of 1,451 g of 100% N,N'-bis(2-hydroxyethyl)oxamide had been collected, corresponding to an average yield of 91.6%.

EXAMPLES 3 to 6

Example 1 was repeated by changing the reaction conditions in accordance with the data recorded in the While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of N,N'-bis(2-hydroxyethyl)oxamide, comprising reacting an alkyl oxalate with ethanolamine in an aqueous reaction medium consisting essentially of water.

2. The process as defined by claim 1, wherein the oxalate is gradually added to an aqueous solution of ethanolamine.

3. The process as defined by claim 1, wherein the temperature of reaction ranges from 0° to 100° C.

4. The process as defined by claim 2, wherein the concentration of ethanolamine in the aqueous solution thereof is at least 2.5 moles per liter of water.

5. The process as defined by claim 4, wherein said concentration is at least 5 moles per liter of water.

6. The process as defined by claim 1, wherein said alkyl oxalate is methyl, ethyl, n-propyl, isopropyl or n-butyl oxalate.

7. The process as defined by claim 1, wherein approximately 2 moles of ethanolamine are provided per mole of said alkyl oxalate.

8. The process as defined by claim 2, wherein said oxalate is added under conditions which substantially avoid hydrolysis of said oxalate.

9. The process as defined by claim 3, wherein the temperature of reaction ranges from 15° to 50° C.

10. The process as defined by claim 1, wherein said N,N'-bis(2-hydroxyethyl)oxamide is recovered directly from said aqueous reaction medium in the form of fine crystals.

11. A process for the preparation of N,N'-bis(2-hydroxyethyl)oxamide, comprising reacting an alkyl oxalate with ethanolamine in an aqueous reaction medium consisting essentially of water, wherein said alkyl oxalate is gradually added to a solution of ethanolamine having a concentration of at least 2.5 moles per liter of water under conditions which substantially avoid hydrolysis of said oxalate, and wherein said N,N'-bis(2-hydroxyethyl)oxamide is recovered directly from said aqueous reaction medium in the form of fine crystals.

* * * * *